US00PP16567P2

(12) United States Plant Patent
Fick

(10) Patent No.: US PP16,567 P2
(45) Date of Patent: May 23, 2006

(54) ***FELICIA* PLANT NAMED 'KING FISHER'**

(50) Latin Name: *Felicia ameloides*
Varietal Denomination: King Fisher

(75) Inventor: Paul Fick, George (ZA)

(73) Assignee: New Plant Nursery, George (ZA)

( * ) Notice: Subject to any disclaimer, the term of this patent is extended or adjusted under 35 U.S.C. 154(b) by 120 days.

(21) Appl. No.: 11/046,032

(22) Filed: Jan. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—C. A. Whealy

(57) ABSTRACT

A new and distinct cultivar of *Felicia* plant named 'King Fisher', characterized by its upright and outwardly spreading plant habit; freely branching growth habit; large inflorescences with relatively broad violet blue-colored ray florets; freely flowering habit; and good garden performance.

1 Drawing Sheet

Botanical designation: *Felicia ameloides*.
Cultivar denomination: King Fisher.

BACKGROUND OF THE INVENTION

The present Invention relates to a new and distinct cultivar of *Felicia* plant, botanically known as *Felicia ameloides*, and hereinafter referred to by the name 'King Fisher'.

The new *Felicia* is a product of a planned breeding program conducted by the Inventor in George, South Africa. The objective of the breeding program is to develop new *Felicia* cultivars with large inflorescences and attractive ray floret coloration.

The new *Felicia* originated from a cross-pollination made by the Inventor in September, 2000 of two unnamed selections of *Felicia ameloides*, not patented. The new *Felicia* was discovered and selected as a single flowering plant by the Inventor in a controlled environment in George, South Africa in August, 2000 from the resultant progeny of the stated cross-pollination. The new *Felicia* was selected on the basis of its unique ray floret coloration.

Asexual reproduction of the new *Felicia* by cuttings was first conducted in George, South Africa in November, 2001. Since then, asexual reproduction by cuttings has shown that the unique features of this new *Felicia* are stable and reproduced true to type in successive generations.

SUMMARY OF THE INVENTION

The cultivar King Fisher has not been observed under all possible enviromental conditions. The phenotype may vary somewhat with variations in environment such as temperature and light intensity without, however, any variance in genotype.

The following traits have been repeatedly observed and are determined to be the unique characteristics of 'King Fisher'. These characteristics in combination distinguish 'King Fisher' as a new and distinct *Felicia:*

1. Upright and outwardly spreading plant habit.
2. Freely branching growth habit.

3. Large inflorescences with relatively broad violet blue-colored ray florets.
4. Freely flowering habit.
5. Good garden performance.

Plants of the new *Felicia* can be compared to plants of the female parent selection. In side-by-side comparisons conducted in George, South Africa, plants of the new *Felicia* differed from plants of the female parent selection in the following characteristics:

1. Plants of the new *Felicia* had larger and darker green-colored leaves than plants of the female parent selection.
2. Plants of the new *Felicia* had larger inflorescences with broader ray florets than plants of the female parent selection.
3. Plants of the new *Felicia* had darker blue-colored ray florets than plants of the female parent selection.

Plants of the new *Felicia* can be compared to plants of the male parent selection. In side-by-side comparisons conducted in George, South Africa, plants of the new *Felicia* differed from plants of the male parent selection in the following characteristics:

1. Plants of the new *Felicia* had longer and darker green-colored leaves than plants of the male parent selection.
2. Plants of the new *Felicia* had larger inflorescences than plants of the male parent selection.
3. Plants of the new *Felicia* had darker blue-colored ray florets than plants of the male parent selection.

Plants of the new *Felicia* can be compared to plants of other nonpatented selections of *Felicia ameloides* known to the Inventor. In side-by-side comparisons conducted in George, South Africa, plants of the new *Felicia* differed from plants of other known selections of *Felicia ameloides* in the following characteristics:

1. Plants of the new *Felicia* grew faster than plants of other known selections of *Felicia ameloides.*
2. Plants of the new *Felicia* had larger leaves than plants of other known selections of *Felicia ameloides.*
3. Plants of the new *Felicia* had larger inflorescences than plants of other known selections of *Felicia ameloides.*

4. Plants of the new *Felicia* had darker blue-colored ray florets than plants of other known selections of *Felicia ameloides*.

BRIEF DESCRIPTION OF THE PHOTOGRAPHS

The accompanying colored photographs illustrate the overall appearance of the new *Felicia* showing the colors as true as it is reasonably possible to obtain in colored reproductions of this type. Colors in the photographs may differ from the color values cited in the detailed botanical description which accurately describe the colors of the new *Felicia*.

The photograph at the top of the sheet comprises a side perspective view of a typical flowering plant of 'King Fisher' grown in a container.

The photograph at the bottom of the sheet is a close-up view of typical inflorescences of 'King Fisher'.

DETAILED BOTANICAL DESCRIPTION

The aforementioned photographs and following observations and measurements describe plants grown in Bonsall, Calif., in an outdoor nursery under full sun conditions during the spring and summer. When the plants were about eight weeks old, the photographs, observations and measurements were taken. Plants used for the detailed description were grown with three plants per 15-cm containers. During the production of the plants, day temperatures ranged from 18 to 35° C. and night temperatures ranged from 10 to 18° C. Color references are made to The Royal Horticultural Society Colour Chart, 1995 Edition, except where general terms of ordinary dictionary significance are used.

Botanical classification: *Felicia ameloides* cultivar King Fisher.

Parentage:

*Female, or seed, parent*.—Unnamed selection of *Felicia ameloides*, not patented.

*Male, or pollen, parent*.—Unnamed selection of *Felicia ameloides*, not patented.

Propagation:

*Type*.—By cuttings.

*Root description*.—Fine, fleshy and freely branching; white, close to 155A, in color.

*Time to initiate roots*.—About ten days.

Plant description:

*Appearance*.—Herbaceous container and garden plant. Upright and outwardly spreading plant habit; hemispherical in shape. Freely branching habit; about three basal branches per plant each with about six laterals. Vigorous growth habit; rapid growth rate.

*Plant height, soil level to top of inflorescences*.—About 36 cm.

*Plant height, soil level to top of foliar plane*.—About 23 cm.

*Plant width or area of spread (single plant)*.—About 21 cm.

*Lateral branches*.—Length: About 20 cm. Diameter: About 3.5 mm. Internode length: About 2.75 cm. Aspect: Upright and outwardly. Strength: Strong. Texture: Pubescent. Color:145A.

*Foliage description*.—Arrangement: Opposite; simple. Length: About 3.5 cm. Width: About 1.7 cm. Shape: Elliptical. Apex: Broadly acute. Base: Attenuate, clasping. Margin: Entire. Texture, upper and lower surfaces: Coarse; glabrous. Color: Developing foliage, upper surface: 144A. Developing foliage, lower surface: 146D. Fully expanded foliage, upper surface: 147A. Fully expanded foliage, lower surface: 147B. Venation, upper surface: 146C. Venation, lower surface: 147C. Petiole: Length: About 5 mm. Diameter: About 6 mm. Texture, upper and lower surfaces: Coarse; glabrous. Color, upper surface: 144B. Color, lower surface: 145C.

Inflorescence description:

*Appearance*.—Terminal inflorescences held above the foliage on long wiry peduncles. Composite inflorescence form, radially symmetrical; elongate oblong-shaped ray florets; disc florets massed at the center; ray and disc florets develop acropetally on the receptacle. Inflorescences persistent. Inflorescences face mostly upright to outwardly.

*Time of flowering*.—Long flowering period; plants flower freely from April through October in Southern California.

*Postproduction longevity*.—Inflorescences maintain good color and substance for about two weeks on the plant.

*Quantity of inflorescences*.—About five to nine open inflorescences and inflorescence buds per lateral stem.

*Fragrance*.—None detected.

*Inflorescence bud*.—Length: About 1.5 cm. Diameter: About 9 mm. Shape: Ovoid. Color: 97B.

*Inflorescence size*.—Diameter: About 3.25 cm. Depth (height): About 1.9 cm. Disc diameter: About 8 mm. Receptacle diameter: About 9 mm. Receptacle height: About 1.1 cm. Receptacle shape: Conical.

*Ray florets*.—Length: About 2.2 cm. Width: About 4 mm. Shape: Linear to elongated oblong. Apex: Emarginate. Base: Attenuate. Margin: Entire. Texture, upper and lower surfaces: Smooth, glabrous; satiny. Orientation: Initially upright and eventually reflexing. Number of ray florets per inflorescence: About 13 in a single whorl. Color: When opening, upper surface: 97B. When opening, lower surface: 97B to 97C. Fully opened, upper surface: 97A; color does not fade with development. Fully opened, lower surface: 97B.

*Disc florets*. —Shape: Elongated tubular. Apex: Five-pointed; acute. Length: About 1.2 cm. Width, apex: About 1 mm. Width, base: Less than 1 mm. Number of disc florets per inflorescence: About 130 massed at the center of the inflorescence. Color: Immature: 6A. Mature, apex: 6A. Mature, mid-section: 155B. Mature, base: Close to 155D.

*Phyllaries*.—Quantity per inflorescence: About 14 in a single whorl. Length: About 1 cm. Diameter: About 1 mm. Shape: Linear. Apex: Acute. Base: Fused to receptacle. Margin: Entire. Texture, upper and lower surfaces: Coarse. Color, upper surface: 144A. Color, lower surface: 146A.

*Peduncles*.—Length, terminal peduncle: About 21 cm. Length, second and third peduncles: About 12 cm. Diameter: About 1 mm. Aspect: Upright to outward. Strength: Strong; wiry. Texture: Coarse; glandular. Color: 144B.

*Reproductive organs*.—Androecium: Present on disc florets only. Stamen number: About five per floret. Anther shape: Elongated oblong. Anther length: About 1.5 mm. Anther color: 19A. Pollen amount: Scarce. Pollen color: 19A. Gynoecium: Present on both ray and disc florets. Pistil number: One per floret. Pistil length: About 1.1 cm. Stigma shape:

Two-parted. Stigma color: 12A. Style length: About 8 mm. Style color: 12C. Ovary color: 157B.

*Seed/fruit*.—Seed and fruit development has not been observed.

Disease/pest resistance: Resistance to pathogens and pests common to *Felicias* has not been observed on plants grown under outdoor conditions.

Garden performance: Plants of the new *Felicia* have been observed to have good garden performance and to tolerate wind and rain. Plants of the new *Felicia* have been observed to tolerate temperatures from −2 to 35° C.

It is claimed:

1. A new and distinct cultivar of *Felicia* plant named 'King Fisher', as illustrated and described.

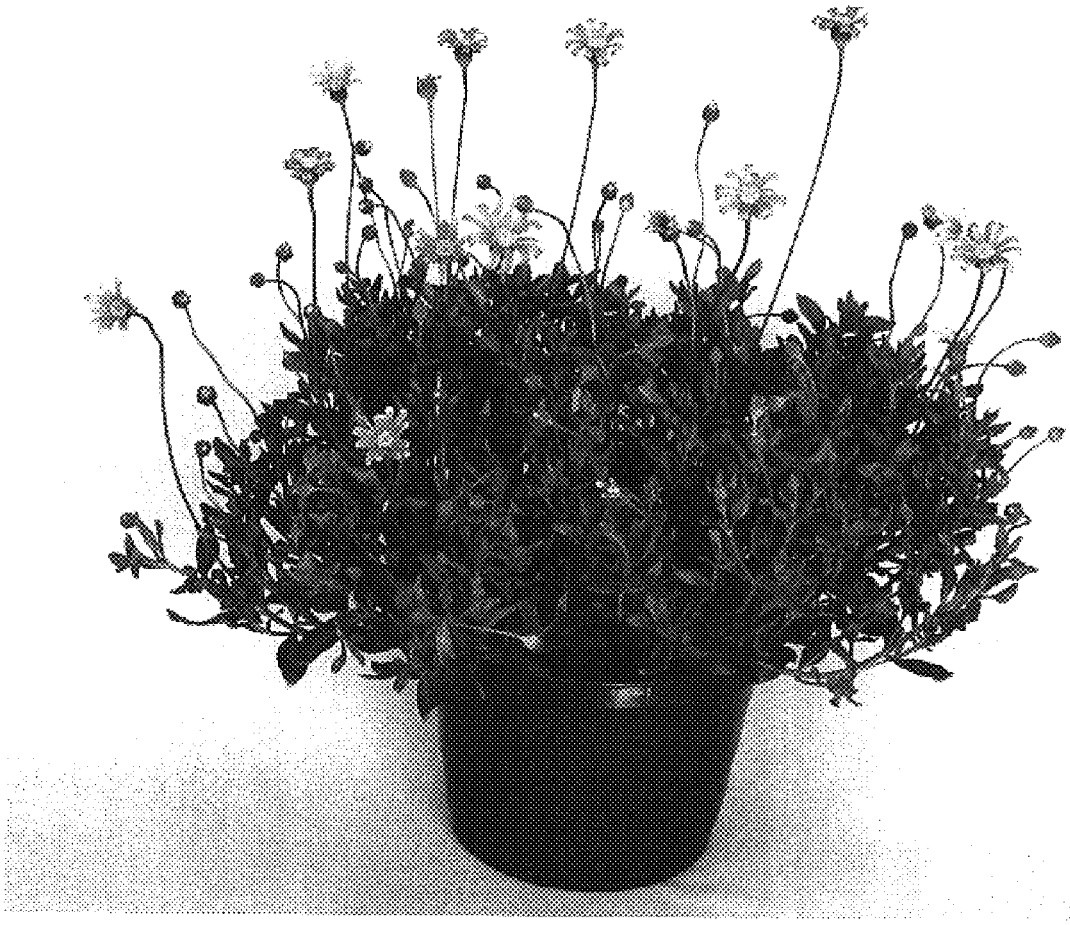
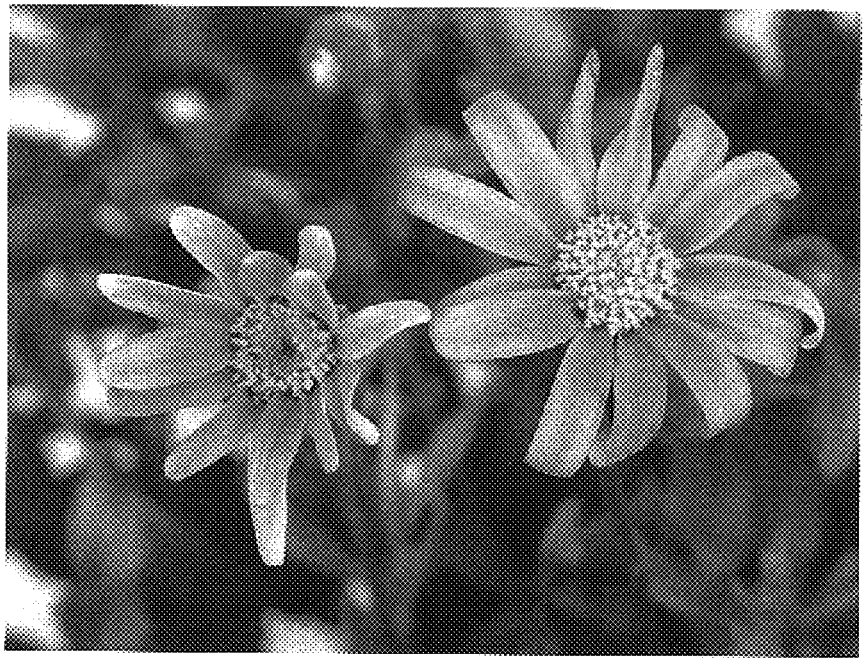

* * * * *